United States Patent
Gullichsen et al.

[11] Patent Number: 5,697,894
[45] Date of Patent: Dec. 16, 1997

[54] DEVICE FOR THE APPLICATION OF TRACTION OR PRESSING FORCE TO THE PATIENT IN THE TREATMENT OF AN INJURED OR DISEASED PART OF THE SUPPORT OR MOTION ORGANS

[76] Inventors: Eero Gullichsen, Jyrätie 3 O, FIN-20540 Turku; Esa Sipola, Haaganmäentie 6, FIN-20460 Turku, both of Finland

[21] Appl. No.: 481,488

[22] PCT Filed: Jan. 17, 1994

[86] PCT No.: PCT/FI94/00018

§ 371 Date: Jul. 11, 1995

§ 102(e) Date: Jul. 11, 1995

[87] PCT Pub. No.: WO94/16651

PCT Pub. Date: Aug. 4, 1994

[30] Foreign Application Priority Data

Jan. 20, 1993 [FI] Finland .................. 930212

[51] Int. Cl.[6] ........................................... A61F 5/00
[52] U.S. Cl. ........................ 602/32; 602/32; 602/36; 602/17; 602/18
[58] Field of Search ................... 602/5, 17–19, 602/32–38; 128/898

[56] References Cited

U.S. PATENT DOCUMENTS

| | | | |
|---|---|---|---|
| 2,904,040 | 9/1959 | Hale | 602/18 |
| 3,724,452 | 4/1973 | Nitschtke | 602/18 |
| 3,776,224 | 12/1973 | McFarland | 602/18 |
| 3,910,263 | 10/1975 | Wallander . | |
| 4,463,750 | 8/1984 | Borschneck | 602/19 |
| 4,539,979 | 9/1985 | Bremer | 602/19 X |
| 4,541,421 | 9/1985 | Iversen et al. | 602/18 |
| 4,632,099 | 12/1986 | Mollo | 602/18 |
| 4,732,144 | 3/1988 | Cunanay | 602/18 |
| 4,807,605 | 2/1989 | Mattingly | 602/19 |
| 4,913,135 | 4/1990 | Mattingly | 602/19 |
| 5,062,415 | 11/1991 | Weatherby et al. | 602/18 X |
| 5,171,296 | 12/1992 | Herman | 602/18 X |
| 5,195,947 | 3/1993 | Bode | 602/18 |
| 5,203,765 | 4/1993 | Friddle, Jr. | 602/18 |
| 5,320,596 | 6/1994 | Catipovic et al. | 602/18 |

FOREIGN PATENT DOCUMENTS

| | | |
|---|---|---|
| 322013 | 9/1966 | Sweden . |
| 334977 | 9/1967 | Sweden . |
| 92/22268 | 12/1992 | WIPO . |

*Primary Examiner*—Linda C. Dvorak
*Attorney, Agent, or Firm*—Kubovcik & Kubovcik

[57] ABSTRACT

An apparatus for applying traction or compression force to a patient in the treatment of an injured or diseased part of a musculoskeletal system, in which a point (b) is situated on a first side of a part to be treated L and a point (a) is situated on an opposite side of part L, point (a) being mobile with respect to point (b). The apparatus includes at least one connecting element R connecting point (a) to a point (p) located on a support. At least one force-transmitting element transmits traction or compression force $F_R$ from a force-applying device to each connecting element R. A control unit, which is connected to a force sensor and an acceleration sensor, controls the force-applying device such that the traction or compression force $F_R$ is adjusted to a value which is sufficient to keep a traction or compression force $F_O$ applied to part L constant and to compensate for any changes in $F_O$ resulting from variation in the inclination of part L relative to the horizontal plane or variation in the inclination of part L relative to each connecting element R, thereby allowing the traction or compression force $F_O$ applied to part L to remain constant while the patient moves relative to the horizontal plane.

13 Claims, 7 Drawing Sheets

DEVICE FOR THE APPLICATION OF TRACTION OR PRESSING FORCE TO THE PATIENT IN THE TREATMENT OF AN INJURED OR DISEASED PART OF THE SUPPORT OR MOTION ORGANS

BACKGROUND OF THE INVENTION

The object of the invention comprises a method and apparatus for the application of traction or compression force to the patient in the treatment of an injured or diseased part of the musculoskeletal system. The invention especially relates to a method and apparatus by which a predetermined traction force can be applied to the patient's cervical spine and maintained unchanged even if the patient's position deviates from the horizontal position.

Particularly diving and road accidents often lead to fractures of the victim's cervical spine caused by the compression or torsion forces acting on the cervical spine. In such accidents the vertebra has been injured or damaged in such manner that requires head traction in the treatment.

Figure 5A:
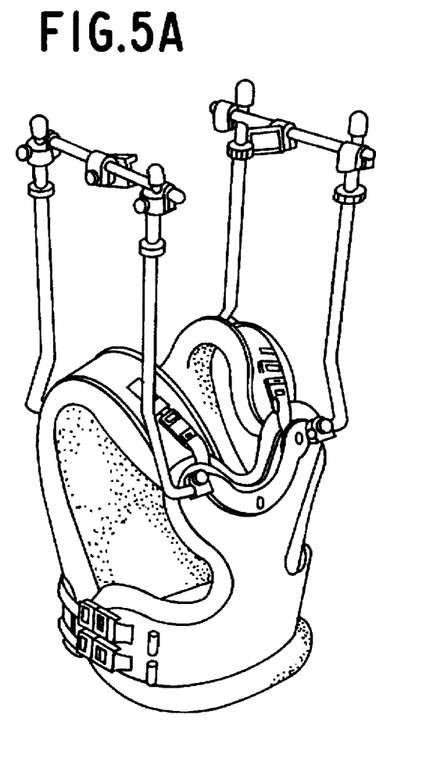
FIGS. 5A-5C show the conventional halo vest device as such and when put on the patient
Figure 5B:
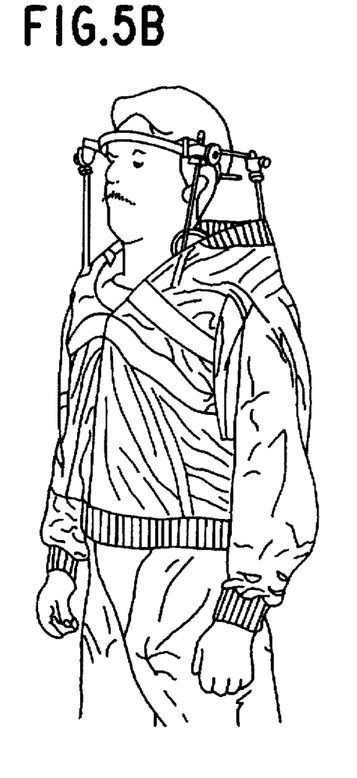
Figure 5C:
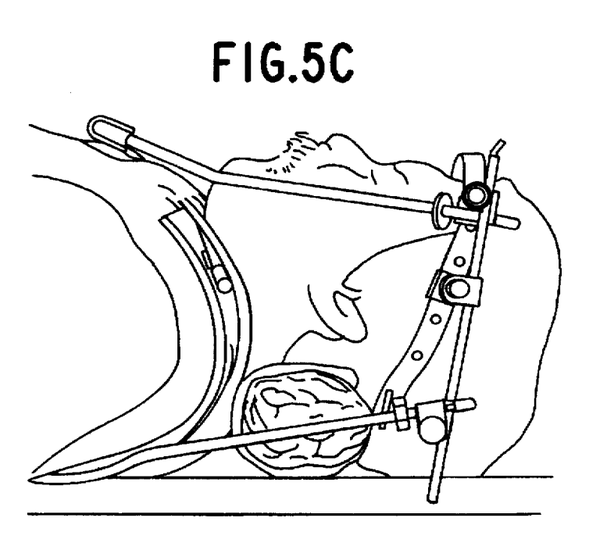

In certain kinds of cervical spine injuries it is possible to apply traction force to the patient's cervical spine by putting a halo vest device on the patient. The halo vest device has a frame resting on the patient's body, which frame is attached by four support rods to a halo ring secured to the patient's head by pins. FIGS. 5A to 5C represent such a halo vest device. With the help of the threads and locking systems of the rods the desired amount of force can be applied between the supporting structure and the halo ring.

If the patient suffers quadriplegia after an accident, the halo vest device described above cannot be applied due to the risk of pressure sores. One treatment method for such patients is to apply classical head traction. In head traction an arc is secured to the patient's head by pins while the patient is lying in the horizontal position, and a traction force is applied to a wire attached to this arc by attaching weights to the descending end of the wire passing over the sheave. The force applied to the patient's cervical spine is regulated by adjusting the amount of weights.

There are several disadvantages in the above-described head traction. The apparatus used is not accurately adjustable and takes up a lot of space with its auxiliary frame. Above all it is inconvenient for the patient and for the nursing staff. The use of the apparatus requires that the patient stays in bed lying on his/her back in a horizontal position for several weeks, even for months. This impairs the patient's physical and mental health. The blood circulation, metabolism and functioning of the intestines suffer especially from the prolonged lying in a horizontal position. The horizontal position also makes nursing the patient, e.g. feeding, washing and physiotherapy very strenuous and time consuming.

SUMMARY OF THE INVENTION

The aim of the present invention is to eliminate the above problems and shortcomings and to present a new method and apparatus for the application of traction or compression force to the patient in the treatment of an injured or diseased part of the musculoskeletal system. The invention relates especially to a method and apparatus by which a predetermined traction force can be applied to the patient's cervical spine and maintained unchanged even if the patient's position deviates from the horizontal position.

The object of the invention thus comprises a method for the application of traction or compression force to the patient in the treatment of an injured or diseased part of the musculoskeletal system, in which a point (b) is situated on the first side of the part to be treated and a point (a) on the opposite side of the part to be treated, (a) being mobile with respect to the point (b), and in which method an essentially constant amount of traction or compression force $F_O$ is applied to the part L between the points (a) and (b). It is characteristic of the method relating to the invention that the point (a) is connected by at least one connecting element R to the point (p) and that such force $F_R$ is applied to the connecting element R that it maintains the above-mentioned constant amount of force $F_O$ and compensates any changes in the force acting on the part treated arising from changed angles between the part treated and the horizontal plane and the changes in the direction of the connecting element R, and thus $F_O$ can be maintained constant even though the patient moves, forming an angle in one or several planes with respect to the horizontal plane.

The invention also comprises an apparatus for the application of traction or compression force to the patient in the treatment of an injured or diseased part of the musculoskeletal system, in which the point (b) is situated on the first side of the part to be treated and the point (a) on the opposite side of the part to be treated, (a) being mobile with respect to the point (b), and by which apparatus an essentially constant amount of traction or compression force $F_O$ is applied to the part L between the points (a) and (b). It is characteristic of the apparatus relating to the invention that it comprises at least one connecting element R by which the point (a) is connected to the point (p) and an element by which such force $F_R$ is applied to the connecting element R that it maintains the above-mentioned constant amount of force $F_O$ and compensates any changes in the force acting on the part treated arising from changed angles between the part treated and the horizontal plane and changes in the direction of the connecting element R, and thus $F_O$ can be maintained constant even though the patient moves, forming an angle in one or several planes to the horizontal plane, and a force applying device, a control and adjustment device, an acceleration sensor, a force sensor, power sources for the force applying device and the control and adjustment device, a force limiter, and possibly a microprocessor in case adjustment is needed in more than one plane with respect to the horizontal plane.

Preferably the desired force $F_O$ is maintained constant in amount and direction with respect to the mentioned points so that the changes in the force acting on the mentioned points are recorded, and on the basis of this information the force applying devices used for maintaining the desired force are controlled, where the apparatus consists of the forces and supporting forces relating to the structures, these forces being adjustable according to the above-mentioned principles.

According to one significant embodiment of the invention, in a method and apparatus relating to the invention, a constant amount of traction force $F_O$ is applied to the patient's cervical spine, this force remaining unchanged even if the patient's position deviates from the horizontal position.

According to an embodiment of the invention, in a method and apparatus relating to the invention, a constant amount of traction force $F_O$ is applied to the patient's cervical spine by applying the invention to a halo vest device. In this embodiment, the point a is connected via an intermediate element V by at least two connecting elements R and R' from attachment points c and c', respectively, on the intermediate element V to points p and p', respectively, on the part B, with part B representing the frame resting on the patient's body, and such compression forces $F_R$ and $F_{R'}$ are applied to the connecting elements R and R' that jointly maintain the above-mentioned constant amount of traction force $F_O$ and which compensate for changes in the forces acting on the cervical spine caused by changes in the angles between the cervical spine and the horizontal plane and possibly changes in the attachment coordinates of the points (p), (p'), (c) and (c'), so that $F_O$ can be maintained constant even though the patient moves, forming an angle in one or several planes with respect to the horizontal plane.

Preferably the apparatus relating to the invention comprises a force applying device, a control and adjustment device, an acceleration sensor, a force sensor, power sources for the force applying device and the control and adjustment device, and a force limiter. In certain embodiments the apparatus also comprises a microprocessor and a sensor measuring angle of swing.

The invention particularly presents a method and apparatus which enable the patient with a cervical spine injury to be freed from lying on his/her back in an unchanged horizontal position by, e.g., adjusting the patient's bed steplessly up to the vertical sitting position with the traction force on the fracture in the cervical spine automatically maintained constant in spite of the change in position.

The embodiment relating to the invention described below is also applicable to devices of halo vest type so that a frame resting on the body is temporarily put on the patient, and one or two support points can be taken on the frame in order to maintain the force on the cervical spine constant even if the patient is moved from the bed to, e.g., a wheelchair.

The embodiment relating to the invention even allows sideways inclinations within certain limits when the patient is in a sitting or half-sitting position without significant changes in the traction force acting on the cervical spine.

The embodiment relating to the invention is particularly significant because it allows more effective rehabilitation measures than the earlier methods, already at an early stage. By altering position, circulatory and metabolic disorders caused by prolonged lying in a horizontal position can be avoided, the risk of pressure sores lessened, and the work of the nursing staff facilitated. The mental health of the patient endures the problems brought by paralysis better, because the weeks-long unbroken period of lying on the back involved in the first stage when using previous methods is avoided.

BRIEF DESCRIPTION OF THE DRAWINGS

The principles of the method and apparatus relating to the invention are exemplified in the following with reference to the accompanying drawings, in which.

DESCRIPTION OF THE PREFERRED EMBODIMENTS

Figure 1:
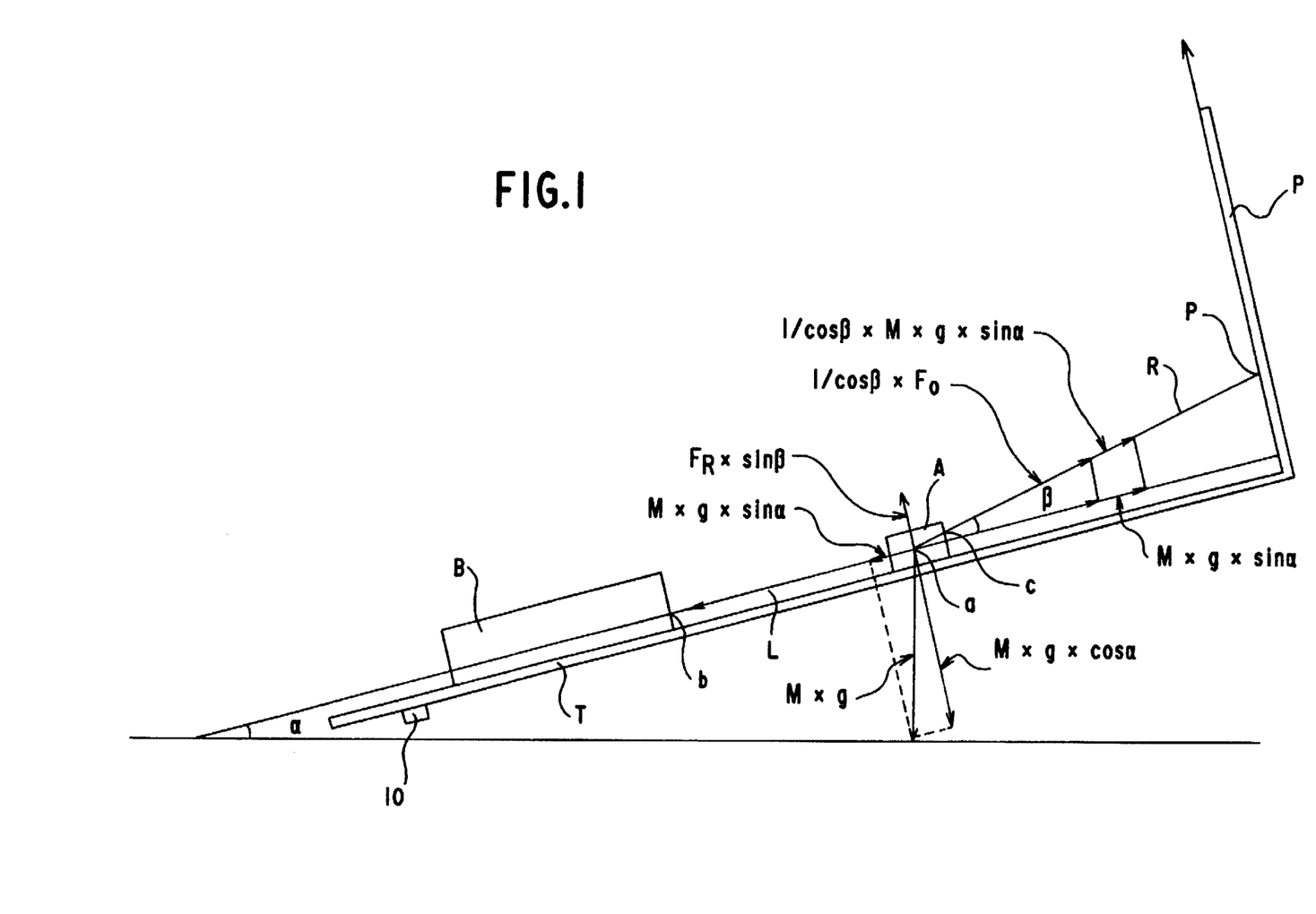
FIG. 1 shows the theoretical basis of the invention as seen from the side of the plane T

FIG. 1 shows in the form of an example the system's parts, static forces and their summing. The inclination of plane T with respect to the horizontal plane may vary within the range of 0° to 90°. The plane P is mounted in a fixed position at an angle of 90° with respect to plane T. Part B is mounted in a fixed position to the plane T. Part A resting without friction on the plane T is supported so that it can move only in line with the straight line drawn from the part B perpendicularly to the plane P. The mass of part A is M, which in a certain embodiment varies typically within the range of 2 to 8 kg. The connecting element L, the length of which may be affected by both traction and compression forces, connects the parts A and B from points a and b. The connecting element R connects part A from the attachment point c to the point p in the end plane P. The attachment point c on the surface of the part A, or in its vicinity, has been selected so that the centre of gravity a of the part A is on the prolongation of the straight line p-c. The direction of the connecting element R may in this model vary from 0° to 20° with respect to the plane T, and from -20° to +20° with respect to the shared perpendicular plane drawn for the planes T and P via parts A and B (see FIG. 2). The acceleration sensor is marked by reference number 10.

Figure 2:
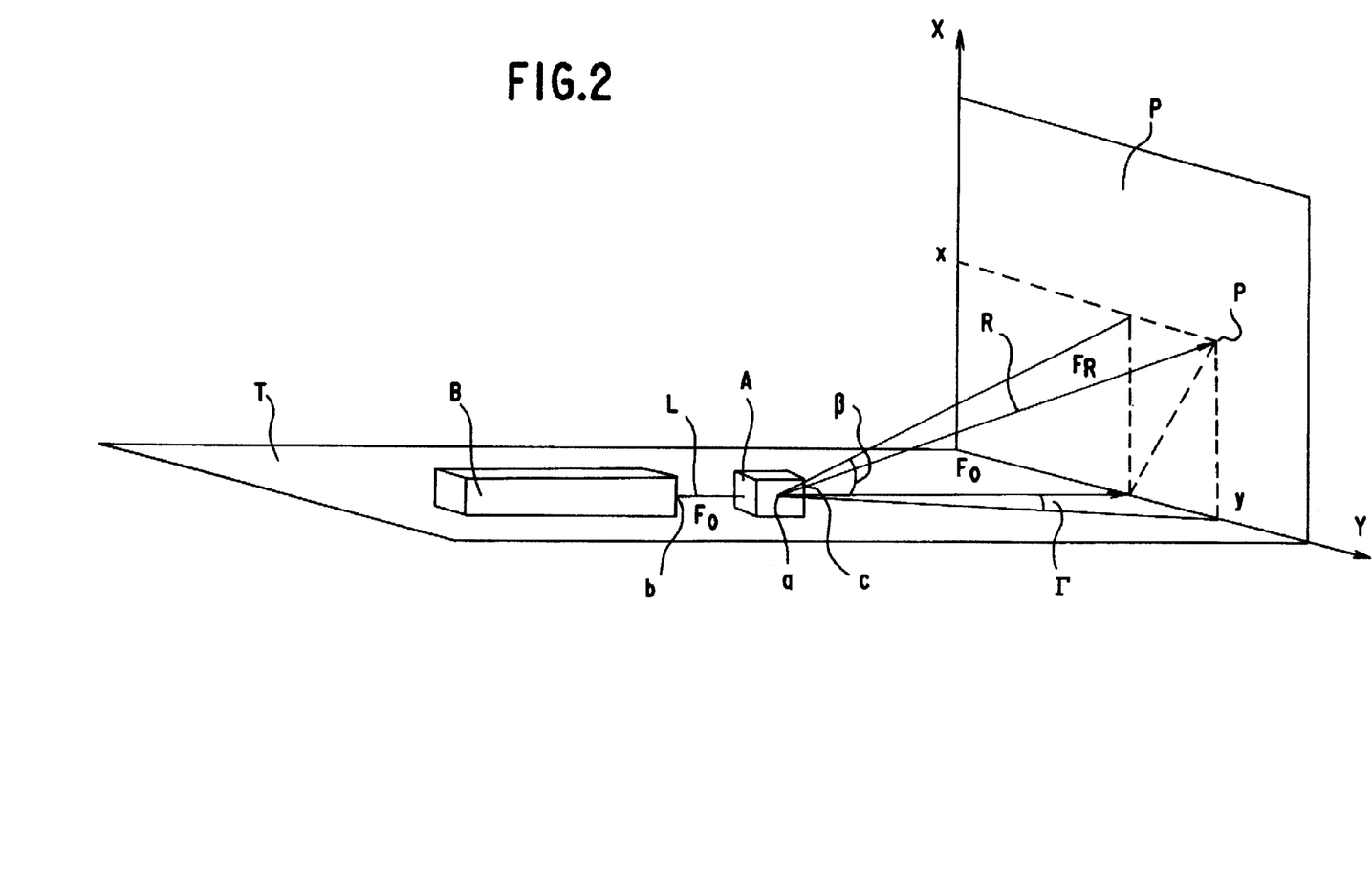
FIG. 2 shows the theoretical basis of the invention, the plane T being represented as a perspective view

One of this system's purposes may be to keep the part A stationary by adjusting the traction force $F_R$ acting on the connecting element R so that the desired amount of force $F_O$ acting on the connecting element L connecting the parts A and B is maintained constant. In the present example $F_O$ may vary within the range of 0.5 to 8 kg. On the basis of FIGS. 1 and 2 it is possible to calculate the force $F_R$ needed for maintaining the force $F_O$ acting on the connecting element L at the desired level. $F_R$ is determined according to the equation (I) below:

$$F_R = (1/\cos(\arctan\sqrt{(\tan^2\beta \times \tan^2\Gamma)})) \times (F_0 + M \times g \times \sin\alpha) \qquad (I)$$

in which equation $\alpha$ is the angle between the plane T and the horizontal plane, $\beta$ is the angle between the projection of the straight line a-p transferred to the perpendicular plane common to the planes T and P going via the point a and the prolongation of the straight line a-b, $\Gamma$ is the angle between the projection of the straight line a-p transferred to the plane T and the prolongation of the straight line a-b, M is the mass of the part A, and g is the acceleration caused by gravity.

In FIG. 2 the inclination of the plane T has not been taken into account because it produces only a force parallel to the plane T if it is assumed that $F_R \times \sin\beta < M \times g \times \cos\alpha$, in other words the part A is not detached from the plane T by the force. The compensation of the force parallel to this plane by the force $F_R$ is dependent only on the angle $\beta$.

In the equation (I) it is possible to replace the term $1/\cos(\arctan\sqrt{(\tan^2\beta \times \tan^2\Gamma)})$ which is dependent on the attachment angles $\beta$ and $\Gamma$, with the product of multiplication of the terms $K_x$ and $K_y$, which terms are dependent on the attachment co-ordinates x and y, the equation thus now taking the form $$F_R = K_x \times K_y \times (F_O + M \times g \times \sin\alpha) \qquad (II)$$

The coefficients can be chosen so that the error in $F_R = 0$ for all values of x and y. For small values (less than 20°) of $\beta$ and $\Gamma$ these can be approximated by coefficients linearly dependent on x and y.

The system described above is applicable to a situation where only the acceleration caused by gravity acts on the part A, and of this only a one-directional component needs to be taken into account. If the situation is made more complex so that acceleration appears in three dimensions, several forces acting in different directions must correspondingly be applied to the part A in order to compensate the changes in the forces on the connecting element L caused by the accelerations. In such a case acceleration is measured in the direction of the axes of an orthogonal system of co-ordinates attached in the direction of the connecting element L. The directions of the compensatory forces are selected so that they are parallel, if possible.

Figure 3:
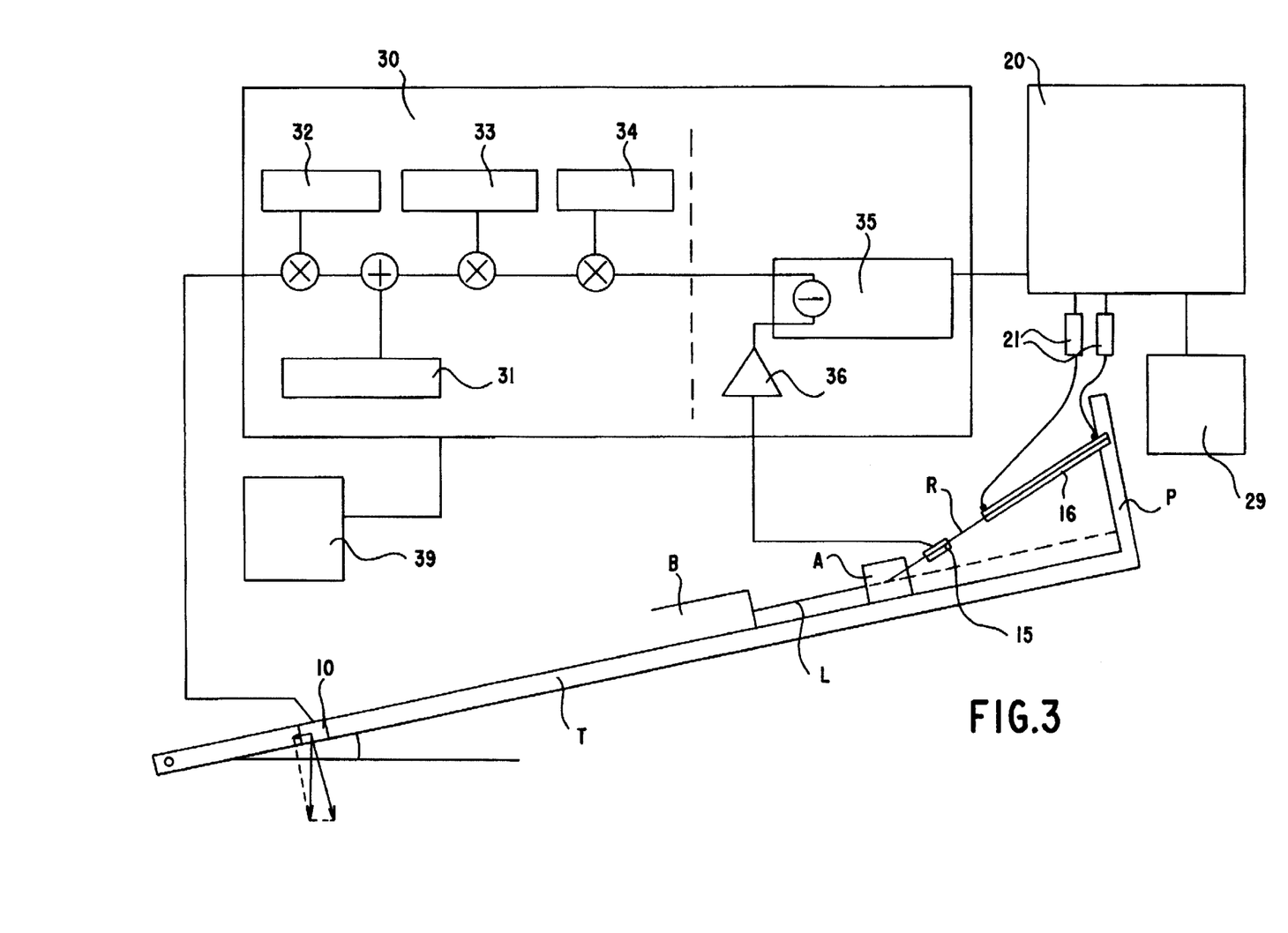
FIG. 3 shows the functional diagram of the apparatus relating to the invention
Figure 4:
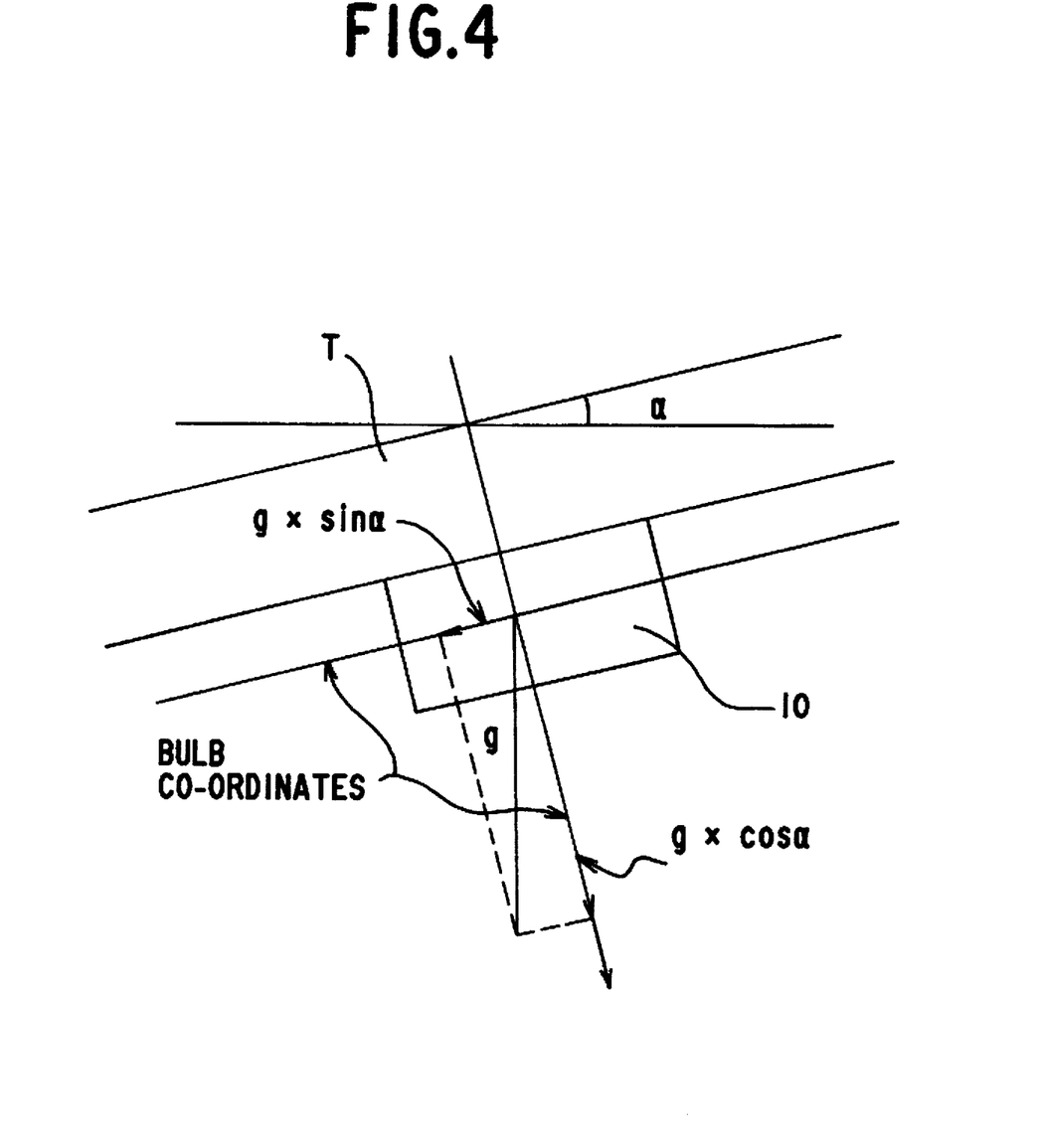
FIG. 4 shows the acceleration sensor connected to the plane T

FIG. 3 shows the functional diagram of the method and apparatus relating to the invention. In practice, first the required settings are made, after which the plane T is inclined to the position desired during the functioning, with the apparatus automatically maintaining the force acting on the connecting element L constant. The force applying device 20, which has been presented as a hydraulic unit in FIG. 3, produces the required force on the connecting element R. The force applying device is controlled by a control electronics unit 30, which receives information about the force $F_R$ via a sensor 15 registering force. In the present example the sensor used is a strain gauge sensor. The sensor is located in a place in which it directly measures force $F_R$ (in the present example, the sensor is located on the arm of the hydraulic cylinder 16).

The information needed by the control electronics on the traction force $F_O$, mass M, coefficients $K_x$ and $K_y$ are given manually (31, 32, 33, 34). In addition the electronics need information g×sinα measured by the acceleration sensor 10 fixed to the plane T. The sensor is placed so that it measures acceleration in the direction of the connecting element L. In such case the acceleration component parallel to the connecting element is proportional to the product of g×sinα.

On the basis of the above-mentioned information, the setting component of the control electronics calculates the setpoint for the controller. The controller 35 compares the setpoint with the signal received from the force sensor and calculates their difference signal. The controller, e.g. a PI-controller, controls the force applying device so that the difference signal is zero. The reference number 36 represents an amplifier.

The coefficients $K_x$ and $K_y$ can also be given automatically to the control electronics by a sensor measuring angle of swing located at the attachment point of the hydraulic cylinder 16 and the plane P (not shown in FIG. 3).

Apparatus includes a force limiter 21 preventing excessive forces from being generated in case of malfunction. In a hydraulically operated force applying device the limiting can be created, e.g., by a pressure limiter in the control hose. The power sources of the force applying device 20 and the electronics unit 30 have been marked by reference numbers 29 and 39, respectively.

If measurements are needed only in one dimension, analog electronics will suffice as adjustment electronics. Also in case measurements are needed in three dimensions analog electronics may be sufficient, if the directions of measurement of compensatory forces and accelerations can be appropriately arranged in practice. If this is not possible, the calculation of forces becomes so complex that a microprocessor should be used in computing.

In a situation where a hydraulic force applying device is used, it is easy to attach the force sensor directly to the arm of the cylinder in which case there will be no difficult-to-handle wiring. The disadvantage in this is, e.g., that the parts A and B can be moved only within the limits of the length of the cylinder. The force can alternatively be generated by, e.g., a stepper motor with a wire wound around sheaves. The advantage in this is the wide range of dynamics, and the disadvantage the difficult-to-handle wiring and deciding where to locate the force sensor. As the third alternative, a force applying device based on pneumatics can be mentioned. Here the advantage is the light weight of the components, while the disadvantage is the limit set by the velocity of sound on the adjustment speed.

There are several commercial alternatives available for force sensors, of which the strain gauge sensor is one preferred alternative.

In case measurements in only one dimension are needed, a sensor measuring only one component of acceleration is sufficient as an acceleration sensor. In case measurements in three dimensions are needed, a sensor measuring acceleration in three mutually perpendicular directions is used.

As a force limiter, depending on the force applying device, e.g. a shear pin, a pressure limiter or a friction limiter can be used.

In FIGS. 1 to 3 the connecting element L represents any injured part of the body in general to which a certain amount of force is to be applied. In FIGS. 1 to 3 the connecting element L is specifically designed to depict the patient's cervical spine to which traction force $F_O$ is to be applied. The part B symbolizes the patient's body and the part A the patient's head. In the above description as well as in all the figures the required traction force $F_O$ is applied to the injured part L by applying the required traction force $F_R$ to the connecting element R, which has been placed so that it forms an angle of more than 90°, preferably in the range of 160° to 180°, with the part L. In certain injuries of the cervical spine a traction deviating to some extent from the longitudinal axis of the patient's body (direction a-b) is required. In such cases, this invention allows selection of suitable co-ordinates for the point p that are not on the prolongation of the straight line a-b.

An alternative method for applying the desired traction force $F_O$ to the part L is to place the connecting element R so that it forms an angle of less than 90° with the part L and to apply compression force equal to the traction force in the previous case to the connecting element R. In this case the connecting element must naturally be rigid enough in order to transmit the compression force.

Figure 6:
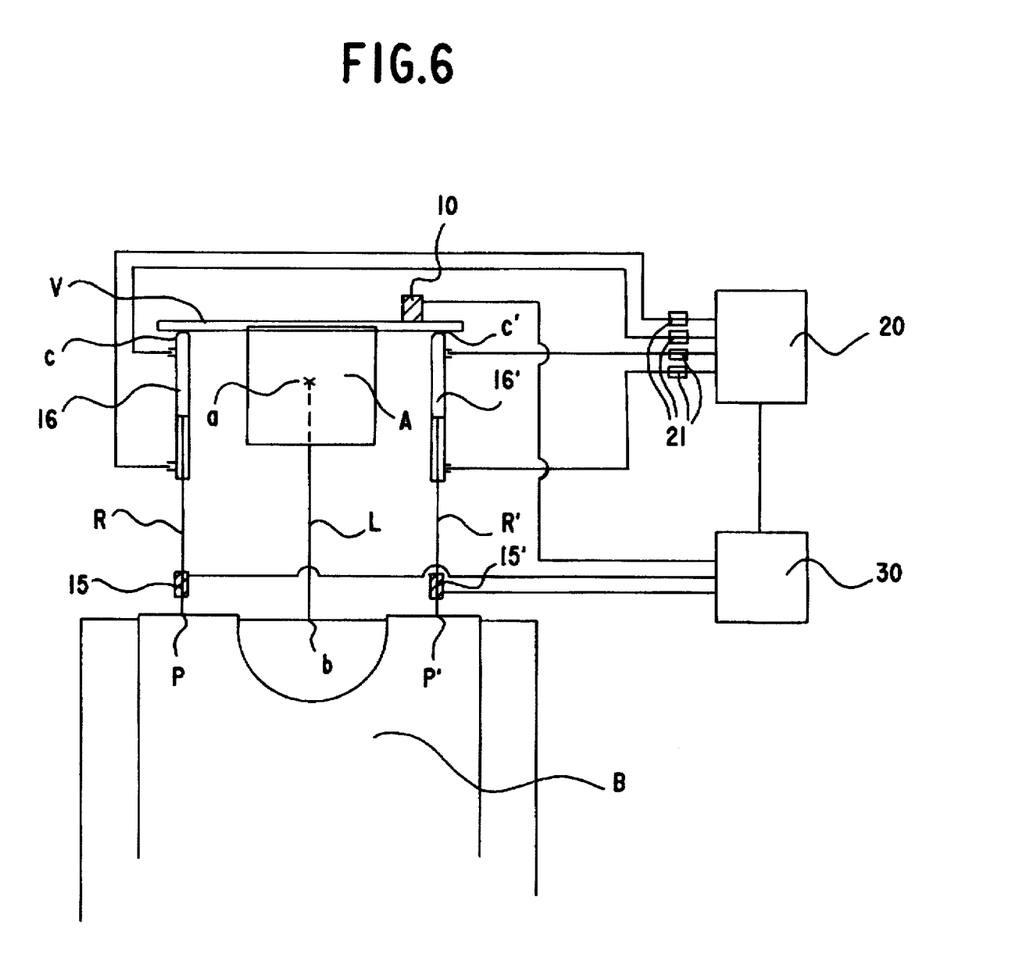
FIG. 6 shows the apparatus relating to the invention applied to halo vest device

FIG. 6 shows the invention when applied to a halo vest device. The centre of gravity of the part A, representing the patient's head, is a, which has been connected via the intermediate element V by two, in this case symmetrically arranged, connecting elements R and R' from the attachment points c and c', respectively, on the intermediate element V to the points p and to p', respectively, on the part B (representing the frame resting on the patient's body, i.e., the halo vest device). Such compression forces $F_R$ and $F_{R'}$ are applied to the connecting elements R and R', which jointly maintain the amount of traction force $F_O$ applied to the patient's cervical spine L constant, and which compensate for the changes in the forces on the cervical spine caused by changes in the angles between the cervical spine and the horizontal plane and possibly in the attachment co-ordinates of the points (p), (p'), (c) and (c'). The reference numbers 16 and 16' refer to the hydraulic or pneumatic cylinders connected to the force applying device 20. The reference numbers 21 represent the force limiters and 15 and 15' refer to the force sensors connected to the controller of the control electronics unit 30. There may of course be three or more connecting elements. The force applying device 20 and the control electronics unit 30 are microprocessor-operated. The sensor measuring angle of swing is marked by number 10.

Figure 7:
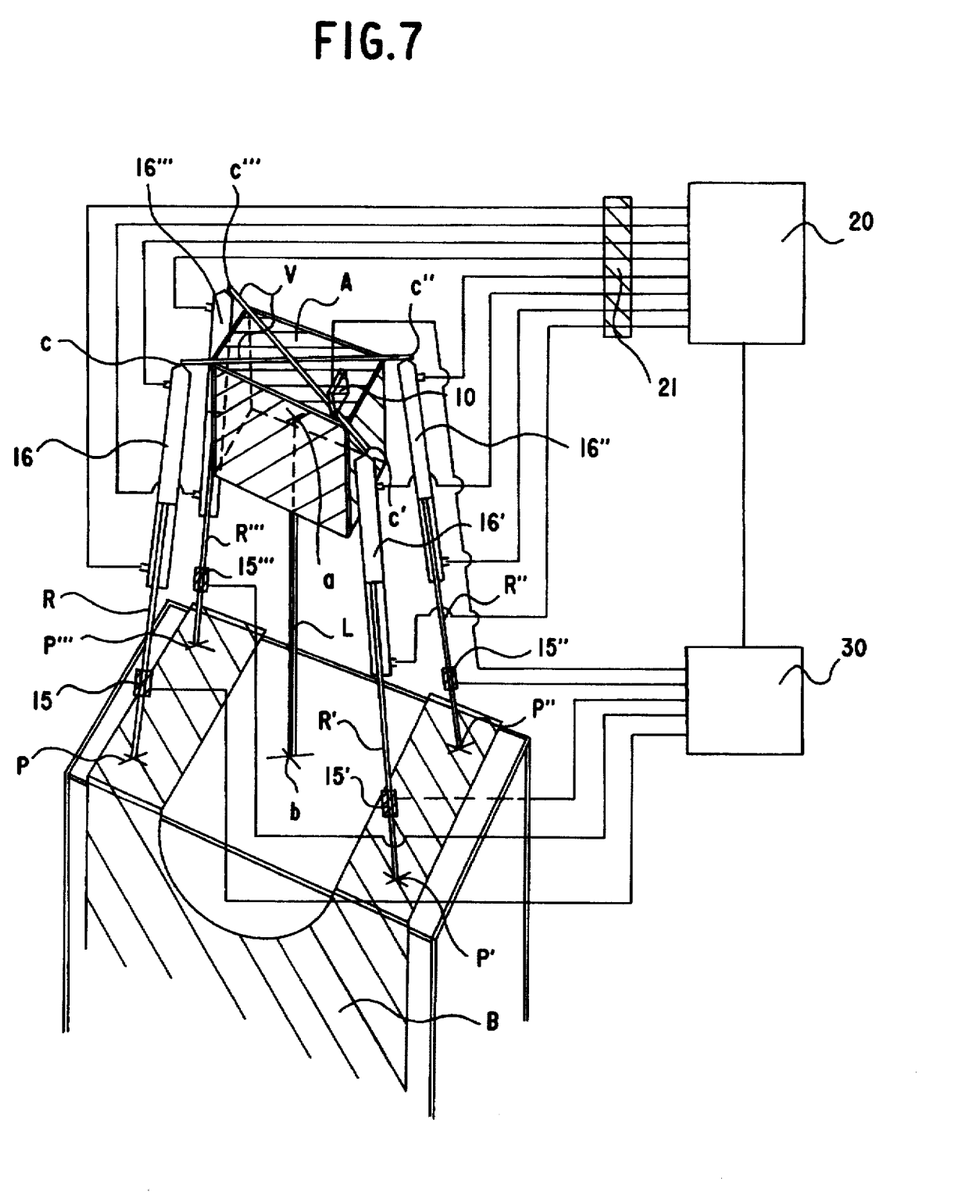
FIG. 7 shows the solution presented in FIG. 6 in a three-dimensional situation

In FIG. 7 a solution according to FIG. 6 is shown in a three-dimensional situation using four connecting elements R, R', R" and R'". In this Figure the quoted reference numbers and letters refer to the same as in FIG. 6 and the apostrophes marked after these indicate which connecting element or attachment point is in question. This Figure shows a solution in which the connecting elements R to R'" are not parallel with cervical spine L but incline slightly towards the cervical spine in the upward direction—this solution corresponds relatively well to the one which would be applied in practice.

If the system is supported, analog electronics is sufficient, but if the system is not supported, a microprocessor is required. The directions, attachment coordinates and support points of the connecting elements are selected so that the force $F_O$ can be uniquely determined.

There are also situations where application of compression force to a part of the patient's body is required. For example, the development of osteoporosis could be stopped if a compression force could be artificially applied to the patient's bone.

The method and apparatus relating to the present invention can also be applied to exerting the desired compression force on the part L of the patient. If, e.g., in a situation relating to FIGS. 1 to 3, in which the connecting element R forms an angle of more than 90° with the part L, compression force is applied to the connecting element R, compression force is exerted on the part L. Correspondingly, if R has been placed with respect to L so that they form an angle of less than 90° to each other, the compression force can be exerted on L by applying traction force to the connecting element R.

The method and apparatus relating to the invention are particularly applicable to the treatment of an injured or diseased part of the patient's skeleton, but it can also be applied more generally in medical rehabilitation directed to the musculoskeletal system.

It is obvious to a person skilled in the art that the different embodiments of the present invention may vary within the scope of the claims presented below.

We claim:

1. An apparatus for applying traction or compression force to a patient in the treatment of an injured or diseased part of a musculoskeletal system, in which a second point (b) is situated on a first side of a part to be treated L and a first point (a) is situated on an opposite side of part L, said first point (a) being mobile with respect to said second point (b), comprising:

at least one connecting element R connecting said first point (a) to a third point (p) located on a support;

at least one force-transmitting element for transmitting traction or compression force $F_R$ to each connecting element R;

a force-applying device for applying force to each connecting element R through each force-transmitting element;

a control unit for controlling said force-applying device, said control unit being connected to said force-applying device;

at least one force limiter for restricting the amount of force transmitted to each force-transmitting element, each force limiter being disposed between said force-applying device and each force-transmitting element;

at least one force sensor for measuring the amount of force $F_R$ being applied by each connecting element R, each force sensor being connected to said control unit;

an acceleration sensor for measuring an angle $\alpha$ between the part L and a horizontal plane, said acceleration sensor being connected to said control unit;

a first power source connected to said force-applying device; and a second power source connected to said control unit, wherein the traction or compression force $F_R$ is adjusted to a value which is sufficient to keep a traction or compression force $F_O$ applied to part L constant and to compensate for any changes in $F_O$ resulting from variation in the inclination of part L relative to the horizontal plane or variation in the inclination of part L relative to each connecting element R, thereby allowing the traction or compression force $F_O$ applied to part L to remain constant while the patient moves relative to the horizontal plane.

2. The apparatus of claim 1, wherein the control unit includes a microprocessor.

3. The apparatus of claim 1, wherein the location of said third point (p) is selected so that a straight line (a)-(b), which is coincident with the part to be treated L, and a straight line (a)-(p), which is coincident with at least one connecting element R, form an angle of more than 90° with respect to each other, and a desired traction force $F_O$ is applied to the part L by applying the required traction force $F_R$ to at least one connecting element R, or a desired compression force $F_O$ is applied to the part L by applying the required compression force $F_R$ to at least one connecting element R.

4. The apparatus of claim 3, wherein the part to be treated L is the patient's cervical spine and said second point (b) is substantially stationary with respect to a plane T on which the cervical spine is supported, the traction force $F_O$ is to be applied to the cervical spine, and the traction force $F_R$ applied to at least one connecting element R is determined according to the equation $$F_R = (1/\cos(\arctan \sqrt{(\tan^2\beta \times \tan^2\Gamma)})) \times (F_0 + M \times g \times \sin\alpha)$$

where $\alpha$ is an angle between the plane T and the horizontal plane, $\beta$ is an angle between a projection of the straight line (a)-(p) transferred to a perpendicular plane common to the plane T and a plane P mounted at an angle of 90° with respect to plane T through said first point (a) and a prolongation of a straight line (a)-(b), $\Gamma$ is an angle between the projection of the straight line (a)-(p) transferred to the plane T and the prolongation of the straight line (a)-(b), said third point (p) is located in plane P, M is the mass borne by the cervical spine, and g is the acceleration caused by gravity.

5. The apparatus of claim 4, wherein the control unit is provided with information about the values of quantities $F_O$, M, $\beta$, and $\Gamma$, information about the angles between the cervical spine and the horizontal plane at any one time as measured by the acceleration sensor, and information about the force $F_R$ acting on at least one connecting element R as measured by the force sensor, and the force measured by the control unit is compared with a guideline value and, if necessary, the control unit causes the applied force $F_R$ to be adjusted.

6. The apparatus of claim 1, wherein the location of said third point (p) is selected so that a straight line (a)-(b), which is coincident with the part to be treated L, and a straight line (a)-(p), which is coincident with at least one connecting element R, form an angle of less than 90° with respect to each other, and a desired traction force $F_O$ is applied to the part L by applying the required compression force $F_R$ to at least one connecting element R, or a desired compression force $F_O$ is applied to the part L by applying the required traction force $F_R$ to at least one connecting element R.

7. The apparatus of claim 6, wherein the part to be treated L is the patient's cervical spine and said second point (b) is substantially stationary with respect to a plane T on which the cervical spine is supported, the traction force $F_O$ is to be applied to the cervical spine, and the compression force $F_R$ applied to at least one connecting element R is determined according to the equation $$F_R = (1/\cos(\arctan \sqrt{\tan^2\beta \times \tan^2\Gamma})) \times (F_0 + M \times g \times \sin\alpha)$$

where $\alpha$ is an angle between the plane T and the horizontal plane, $\beta$ is an angle between a projection of a straight line (a)-(p) transferred to a perpendicular plane common to plane T and a plane P mounted at an angle of 90° with respect to plane T through the point (a) and a straight line (a)-(b), $\Gamma$ is an angle between the projection of the straight line (a)-(p) transferred to the plane T and the straight line (a)-(b), said second point (p) is located in plane P, M is the mass borne by the cervical spine, and g is the acceleration caused by gravity.

8. The apparatus of claim 7, wherein the control unit is provided with information about the values of quantities $F_O$, M, $\beta$, and $\Gamma$, information about the angles between the cervical spine and the horizontal plane at any one time as measured by the acceleration sensor, and information about the force $F_R$ acting on at least one connecting element R as measured by the force sensor, and the force measured by the control unit is compared with a guideline value and, if necessary, the control unit causes the applied force $F_R$ to be adjusted.

9. The apparatus of claim 1, wherein the part to be treated L is the patient's cervical spine to which an essentially constant amount of traction force $F_O$ is to be applied, and said first point (a) is connected via an intermediate element by at least two connecting elements R and R' from first attachment point (c) and second attachment point (c'), respectively, on said intermediate element to said third point (p) and a fourth point (p') on a frame resting on the patient's body, and compression forces $F_R$ and $F_{R'}$ are applied to connecting elements R and R' to maintain said traction force $F_O$ and are adjusted to compensate for changes in the forces acting on the cervical spine resulting from changes in the angles between the cervical spine and the horizontal plane or changes in the coordinates of said third point (p), said fourth point (p'), said first attachment point (c), and said second attachment point (c') so that said traction force $F_O$ can be held essentially constant while the patient moves relative to the horizontal plane.

10. The apparatus of claim 9, wherein the control unit is provided with information about the values of quantities $F_O$ and M, and the coordinates of said third point (p), said fourth point (p'), said first attachment point (c), and said second attachment point (c'), information about the angles between the cervical spine and the horizontal plane at any one time as measured by the acceleration sensor, and information about the force $F_R$ acting on the connecting element R and the force $F_{R'}$ acting on the connecting element R' as measured by force sensors, and the forces measured by the control unit are compared with guideline values and, if necessary, the control unit causes the applied forces $F_R$ and $F_{R'}$ to be adjusted.

11. The apparatus of claim 10, further comprising a sensor measuring angle of swing for the automatic feeding of $\beta$, $\Gamma$, or the coordinates of said third point (p), said fourth point (p'), said first attachment point (c), and said second attachment point (c') into the control unit.

12. The apparatus of claim 10, wherein the force-applying device is a hydraulic unit.

13. The apparatus of claim 10, wherein the force-applying device is a pneumatic unit.

* * * * *